United States Patent [19]

Close et al.

[11] Patent Number: 5,774,521
[45] Date of Patent: Jun. 30, 1998

[54] REGULARIZATION TECHNIQUE FOR DENSITOMETRIC CORRECTION

[75] Inventors: Robert Alan Close, Manhattan Beach; James Stuart Whiting, Los Angeles, both of Calif.

[73] Assignee: Cedars-Sinai Medical Center, Los Angeles, Calif.

[21] Appl. No.: 676,735

[22] Filed: Jul. 8, 1996

[51] Int. Cl.$^6$ .................................................. G01N 23/04
[52] U.S. Cl. ......................................... 378/62; 378/98.4
[58] Field of Search ............................ 378/62, 98.4, 901

[56] References Cited

U.S. PATENT DOCUMENTS

| | | | |
|---|---|---|---|
| 5,376,795 | 12/1994 | Hasegawa et al. | 250/363.04 |
| 5,533,088 | 7/1996 | Fivez | 378/98.4 |
| 5,602,895 | 2/1997 | Fivez et al. | 378/98.4 |

OTHER PUBLICATIONS

R.A. Close, J.S. Whiting, Regularization Method for Scatter–Glare Correction, Medical Physics, vol. 22, No. 6, Jun. 1995.

S. Naimuddin, B. Hasegawa, C.A. Mistretta, Scatter–Glare Correction Using a Convolution Algorithm with Variable Weighting, Med. Phys. 14(3), 330–334 (1987).

J.A. Siebert, O. Nalcioglu, W. Roeck, Removal of Image Intensifier Veiling Glare By Mathematical Deconvolution Techniques, Med. Phys. 12(3), 281–288 (1985).

L. A. Love, R. A. Kruger, Scatter Estimation for a Digital Radiographic System Using Convolution Filtering, Med. Phys. 14(2), 178–185 (1987).

J.A. Seibert, J.M. Boone, X–Ray Scatter Removal By Deconvolution, Phys. Med. 15(4), 567–575 (1988).

J.A. Seibert, O. Nalcioglu, W.W. Roeck, Characterization of the Veiling Glare PSF in X–Ray Image Intensified Fluoroscopy, Med. Phys. 11(2), 172–179 (1984).

S.Y. Mollio, C.A. Mistretta, Scatter–Glare Corrections in Quantitative Dual–Energy Fluoroscopy, Med. Phys. 15(3), 289–297 (1988).

C.M. Fivez, P. Wambacq, P. Suetens, E. Schoeters, A Linear Model For the Scattered Radiation Distribution in Digital Chest Radiographs, SPIE vol. 2708, 128–139 (Feb. 11, 1996).

S. Molloi, G. Wamsleey, Y. Zhou, Scatter–Glare Estimation for Quantitative Cardiac Imaging, SPIE vol. 2708, 150–156 (Feb. 11, 1996).

R.A. Close and J.S. Whiting, Regularization Technique for Restoration of X–Ray Fluoroscopic Images, SPIE vol. 2570, 145–150 (Jul. 10, 1995).

*Primary Examiner*—David P. Porta
*Assistant Examiner*—David Vernon Bruce
*Attorney, Agent, or Firm*—Loeb & Loeb LLP

[57] ABSTRACT

Method and apparatus for scatter-glare correction in x-ray diagnostic images from a patient. A reference object placed between the x-ray source and the subject is imaged in superposition with the subject without completely blocking any area of the subject image. The density distribution of the reference object is designed to have very small spatial correlation with the density distribution of the subject. The scatter-glare component is modeled by convoluting the primary component with a parameterized response function. During post-processing of the digital image, the unknown parameters of the response function are adjusted to minimize a cost function based on the expectation that the correlation between the reference object and the subject should be small and that the values of the parameters not deviate significantly from the estimated values for a typical patient. The scatter-glare component of the subject and the reference object, as well as the image of the reference object, are subsequently subtracted from the raw image to yield the image of the subject free of scatter-glare effects.

22 Claims, 2 Drawing Sheets

REGULARIZATION TECHNIQUE FOR DENSITOMETRIC CORRECTION

BACKGROUND OF THE INVENTION

1. Field of the Invention

The present invention relates to scatter-glare correction for x-ray desitometry using deconvolution techniques, and in particular to deconvolution techniques using a calibration phantom and a regularization technique.

2. Description of the Prior Art

X-ray imaging is widely used in medical diagnostics and other fields of application. However, an x-ray image obtained from a subject such as a patient is degraded by many factors resulting in artifacts in the image. For example, an x-ray image of a patient is degraded by x-ray scattering within the patient. As a result of this scattering, the image obtained using an x-ray detector is a superposition of a primary component, or the image of the subject, and a scattered component associated with the primary component. In x-ray fluoroscopy where an image intensifier is used in front of the x-ray detector, images are further degraded by veiling glare in the image intensifier. Veiling glare arises from the scatter of electrons and photons within the x-ray image intensifier and causes the electrons and photons produced from the brighter areas of the image to be spread into the darker areas, resulting in a blurring of the image.

These artifacts must be corrected before accurate quantitative information can be derived from the images. Various post-processing techniques have been developed to remove the scatter and glare effects from recorded x-ray images, such as deconvolution. Deconvolution techniques employ a convolution model to describe the scatter-glare component. Mathematically, the scatter-glare component of an image can be modeled by a spatial convolution of the primary component with a two-dimensional response function. When the response function is known, an estimate of the primary component of the image can be calculated from the measured image intensities by a deconvolution technique (also known as Wiener filtering or constrained restoration). Scatter-glare correction using deconvolution techniques is described in, for example, J. A. Seibert et al., *Removal of Image Intensifier Veiling Glare by Mathematical Deconvolution Techniques*, MED. PHYS., 12(3), 281–288 (1985); S. Naimuddin et al., *Scatter-Glare Correction Using a Convolution Algorithm with Variable Weighting*, MED. PHYS., 14(3), 330–334 (1987); L. A. Love et al., *Scatter Estimation for a Digital Radiographic System Using Convolution Filtering*, MED. PHYS., vol. 14(2), 178–185 (1987); L. A. Seibert et al., *X-ray Scatter Removal by Deconvolution*, MED. PHYS., 15(4), 567–575 (1988); and *Scatter-Glare Corrections in Quantitative Dual-Energy Fluoroscopy*, MED. PHYS., 15(3), 289–297 (1988). Various functions may be used for the response function, such as exponential or Gaussian functions. The parameters of a response function are usually determined empirically. Ideally, because the response function for each image is dependent upon various acquisition parameters such as beam energy, imaging geometry and patient thickness, which are variable from patient to patient, the precise response function parameters should be determined for each individual patient to achieve accurate scatter-glare removal.

Various methods for determining the response function parameters have been developed. In the methods described in the above references, the response function parameters are estimated by using an object such as a Lucite slab to mimic a patient, placing a series of lead objects before the Lucite object to completely block the direct x-rays in parts of the image, and measuring the x-ray intensities in the blocked areas of the image which presumably consist solely of the scatter-glare component. These methods only give the estimated parameters for an average or typical patient.

To account for dependence of the response function parameters on acquisition parameters, one deconvolution method allows variation of the response function parameters based on empirical relationships between the acquisition parameters and the response function parameters. However, this method still does not allow response function parameters to be optimized for each individual patient. In another method, an array of beam stops is placed between the x-ray source and the patient when the patient is being imaged to block the direct x-ray, and the response function parameters for the particular patient are determined by comparing the image intensities behind the beam stops (which presumably would be scatter-glare only) with scatter-glare intensities calculated from the convolution model. A disadvantage of this method is a loss of information due to complete blocking of parts of the image. Other techniques involve taking multiple images of the patient, such as with and without beam stops, to estimate the parameters. These methods suffer the disadvantage of increased patient radiation dose and data acquisition time.

Thus, each of these methods suffers one or more of the following disadvantages: (1) the response function parameters are not optimized for each individual patient being imaged, thus reducing the accuracy of the scatter-glare removal; (2) more than one image must be taken to obtain one corrected image, thus increasing patient radiation dose and the length of the x-ray process, and reducing throughput in the x-ray process; (3) the image of the patient is completely blocked in some areas by beam stops or other lead objects placed in the beam. These and other disadvantages often make these techniques unsuitable for clinical applications.

Therefore, it is an object of the present invention to provide a method and apparatus for scatter-glare correction for x-ray images suitable for clinical applications. It is another object of the present invention to provide a method and apparatus for scatter-glare correction without requirements of specific prior knowledge about the subject. It is a further objective of the present invention to provide a post-processing method for scatter-glare correction for a single x-ray image without the need for multiple images. It is yet a further objective of the present invention to provide a method and apparatus for scatter-glare correction without using beam stops or other objects that block parts of the subject image.

SUMMARY OF THE INVENTION

These and other objectives are achieved by the preferred embodiments of the present invention. According to a preferred embodiment, a reference object is placed between the x-ray source and the subject and imaged in superposition with the subject. The density distribution of the reference object is designed to have very small spatial correlation with the density distribution of the subject. The scatter-glare component is modeled by a convolution of the primary component with a parameterized response function. During post-processing of the image, the unknown parameters of the response function are adjusted to minimize a cost function based on the expectation that the correlation between the reference object and the subject should be small. As a result of the post-processing, the scatter-glare component of the subject and the reference object, as well as the reference object image, are removed from the raw image and an image of the subject free of scatter-glare effects is obtained.

More particularly, a densitometric calibration phantom having a known spatial density distribution is placed in the x-ray beam while the x-ray image of a subject is being taken. The calibration phantom produces on the recorded x-ray image a primary image of the phantom and an associated scatter-glare component, which are superimposed on the primary image and the scatter-glare component produced by the subject. The densities of the calibration phantom is sufficiently low so that it does not completely block any part of the subject image. The density distribution of the phantom is designed such that the spatial correlation of the gird density and the subject density is very small. The x-ray image is digitized, and the digital image is processed numerically using a regularization technique as follows.

The scatter-glare component in the observed x-ray image is modeled by a spatial convolution of a parameterized response function with a primary component, which represents the density of the x-ray absorbing entities in the x-ray path, such as the subject and the calibration phantom. The parameterized response function used in the convolution has a known form, but contains parameters that are not known prior to processing of the x-ray image. If the statistical noise in the x-ray image is neglected, an estimate of the subject density may be calculated from the measured image intensities, the known calibration phantom density, and a set of estimated response function parameters. By adjusting the values of the estimated parameters to minimize a cost function, the optimum response function parameters can be determined. The scatter-glare component of the subject and the calibration phantom can then be calculated and removed along with the primary image of the calibration phantom to produce a subject image free of scatter-glare components.

Further, other artifacts that affect the x-ray image quality, such as beam hardening, and image blurring due to finite x-ray aperture size, can also be corrected using the regularization technique. This may be done by modeling these effects and including the model parameters in the cost function to be optimized.

The regularization technique may be numerically implemented in computer programs in the disclosed manner. A computer may perform minimization of the cost function, obtain the optimum parameter values, and subtract the scatter-glare component of the subject as well as the primary and the scatter-glare components of the phantom from the digitized image. The digital image so processed may be reproduced graphically on a CRT display or as a photographic image for visualization, or displayed in other formats for further processing.

DETAILED DESCRIPTION OF THE PREFERRED EMBODIMENT

Figure 1:
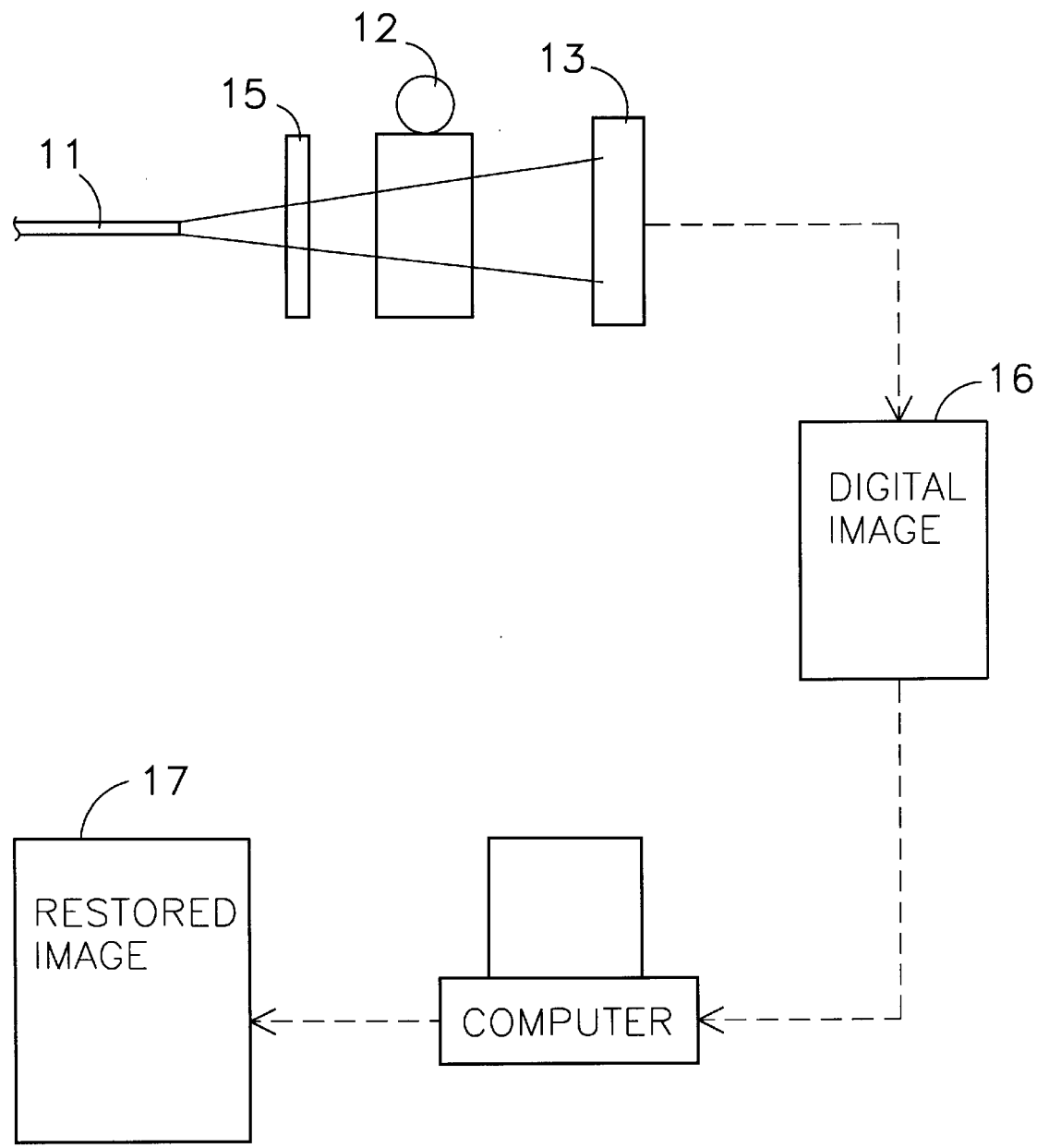
FIG. 1 is a schematic diagram of the apparatus of a preferred embodiment of the present invention.

FIG. 1 is a schematic illustration of a method for recording and correcting an x-ray image of a subject using a reference object according to a preferred embodiment of the present invention. An x-ray source 11 forms an x-ray image of a subject 12 on an x-ray detector 13. The x-ray source, such as an x-ray tube, and the x-ray detector, such as a TV camera or a CCD camera coupled with an x-ray image intensifier, are well known in the art. A calibration phantom 15 is placed between the x-ray source and the detector as a reference object. The calibration phantom absorbs x-rays and produces an image on the x-ray detector, but does not completely block any area of the subject image. The phantom may be constructed from a plate of appropriate x-ray absorbing material, preferably tin, by drilling a depression of controlled depth at each pixel. The x-ray image obtained on the x-ray detector contains an image of the subject 12 and the calibration phantom 15, as well as blurred components generated by x-ray scattering and veiling glare in the image intensifier. The x-ray image is digitized using conventional technology to produce a digital representation of the image 16, which is subsequently processed using a novel regularization technique to remove the effects of scatter and glare and to produce a restored image 17 of the subject.

The processing of the digitized x-ray image requires an understanding of the effects of the system on the digitized image. Empirically, the observed x-ray image 16 includes a primary component, a scatter-glare component, an offset, and random statistical noises. The primary component P is produced by x-ray attenuation by the subject and the calibration phantom as follows:

$$P = I_0 e^{-\rho_s} e^{-\rho_c} \tag{1}$$

where $I_0$ is the incident x-ray intensity from the x-ray source, and $\rho_s$ and $\rho_c$ are the spatial x-ray density distributions of the subject and the calibration phantom, respectively. X-ray density is defined here as the negative logarithm of x-ray attenuation by the respective objects. The density distribution of an object is a two-dimensional distribution defined in a desired plane substantially perpendicular to the x-ray beams, where the density is integrated in the third dimension, or the direction of the x-ray beams. The density distributions $\rho_s$ and $\rho_c$ used in equation (1) are defined in the image plane, so that they include any relative magnification or blurring of the actual objects due to the finite x-ray aperture size. The effects of magnification and blurring will be discussed in more detail below. While the x-ray density of the object $\rho_c$ is known, $\rho_s$ is generally unknown and must be derived.

The scatter-glare component of the image is modeled as a convolution of the primary component with a response function H parameterized by one or more parameters $\sigma_0$. The response function H is preferably Gaussian or exponential. The total observed image intensity $I(x,y)$ is thus given by:

$$I = P + \alpha_0 H(\sigma_0) * P + \beta_0 + N, \tag{2}$$

where $\alpha_0$ is a proportional constant, $\beta_0$ is the offset component, and N is the random statistical noise. The offset may arise from internal noise in the x-ray detector, such as dark currents. The statistical noise arises from the fact that the observed x-ray intensities are produced by a finite number of photons striking on the detector. The nature of these noises are well understood by those skilled in the art. By taking the spatial Fourier transform of equation (2), solving for P by taking the inverse Fourier transform, substituting equation (1) for P, and taking the natural logarithm of the resulting equation, we have:

$$\ln\left[\Im^{-1}\left(\frac{I' - \beta_0\delta(k) - N'}{1 + \alpha_0 H'(\sigma_0)}\right)\right] = \ln(I_0) - \rho_s - \rho_c \quad (3)$$

where the primes (') refer to the spatial Fourier transform of the respective functions of the image intensity, noise and the response function, k is the spatial frequency, δ represents a delta function which is the Fourier transform of a constant function, and $F^{-1}$ represents the inverse Fourier transform. Equation (3) is exact if the values of parameters $\alpha_0$, $\beta_0$ and $\sigma_0$ are known.

Generally, the values of these parameters are unknown and are approximated by a set of values α, β and σ, and the estimate of the subject density is:

$$\hat{\rho}_s(\alpha,\beta,\sigma) = \ln(I_0) + \hat{\rho}_p(\alpha,\beta,\sigma) - \rho_c, \quad (4)$$

where $$\hat{\rho}_p(\alpha,\beta,\sigma) = -\ln\left[\Im^{-1}\left(\frac{I' - \beta\delta(k) - N'}{1 + \alpha H'(\sigma)}\right)\right] \quad (5)$$

is a quantity calculated from the measured x-ray intensities I, noise N and estimated parameter values α,β and σ. Since the incident x-ray intensity $I_0$ is assumed to be spatially uniform but unknown in value, only the spatially non-uniform component of the subject density $\rho_s$ can be estimated:

$$\tilde{\rho}_s(\alpha,\beta,\sigma) = \tilde{\rho}_p(\alpha,\beta,\sigma) - \tilde{\rho}_c \quad (6)$$

where the tilde symbol (~) indicates the difference from the mean value. The constant term $\ln(I_0)$ in equation (4) drops out from equation (6).

When the incident x-ray intensity is sufficiently strong, the statistical noise N will be much smaller than the image intensities I, and may thus be neglected in the regularization technique of the preferred embodiment. When the noise term N' is neglected, the above equation (6) gives the estimate of the non-uniform component of the subject density $\rho_s$ calculated from the measured image intensities I, the known phantom density $\rho_c$, and a set of estimated parameters α,β and σ.

The convolution theory for the scatter-glare effects has been described above. To correct for such effects, the spatial correlation (or the lack of thereof) between the subject density and the calibration phantom is used.

The correlation coefficient between the density distributions of the subject $\rho_s$ and the calibration phantom $\rho_c$ is defined as $$C(\rho_s, \rho_c) = \frac{\Sigma \tilde{\rho}_s \tilde{\rho}_c}{(\Sigma \tilde{\rho}_s^2 \Sigma \tilde{\rho}_c^2)^{\frac{1}{2}}} \quad (7)$$

where the summation is over all the pixels in the interested region of the image.

In the preferred embodiment, the calibration phantom is designed such that the phantom density $\rho_c$ is spatially uncorrelated to the subject density $\rho_s$; i.e., $C(\rho_s,\rho_c) \approx 0$. Preferably, the phantom density is such that it is uncorrelated to any subject density typically seen in actual medical applications. Various designs of such phantom densities are possible. In the preferred embodiment, the phantom density is a constant term (based upon the uniformly thick layer of tin) plus uncorrelated Gaussian distributed random noise (based on the depressions drilled in the tin) having a flat power spectrum of spatial frequencies (up to the highest frequency which is the inverse pixel size) and nearly uniform local variance. Thus, the noise at each pixel of the phantom is preferably a random number having a Gaussian distribution and a variance that is uniform for all pixels.

The ensemble mean correlation coefficient for such calibration phantoms with any signal density is zero as a result of the distribution being Gaussian, and the ensemble variance is $$<|C|^2> = \left\langle \left|\frac{\Sigma \tilde{\rho}_s \tilde{\rho}_c}{(\Sigma \tilde{\rho}_s^2 \Sigma \tilde{\rho}_c^2)^{\frac{1}{2}}}\right|^2 \right\rangle \approx \frac{1}{n}, \quad (8)$$

where n is the number of pixels in the image region of interest. If a large number of pixels are considered, then this variance is extremely small.

The correlation condition in equation (8) is incorporated in the regularization technique of the preferred embodiment as a part of the cost function used for minimizing scatter effects. The theoretical mean expected value of $|C|^2$ (the square of the correlation coefficient between the calibration phantom and the estimated subject density) is $1/n$. Empirically, this value may be determined for a particular calibration phantom by averaging measured correlations between the phantom and typical subject images in which scatter-glare component of the subject has been removed using other techniques, such as by using beam stops. Since the mean expected value of the square of the correlation coefficient $|C|^2$ for a particular calibration phantom is a property of the phantom, this value only needs to be determined once for each phantom and is then used in the regularization process for subsequent images.

In the convolution model for image formation described above, equation (6) relates $\rho_s$, the estimated non-uniform component of the subject density distribution, to the known object density $\rho_c$, the measured image intensity I and the estimated parameters α,β, and σ, the random statistical noise N having been neglected. Since this convolution constraint applies at each of the n pixels, equation (6) gives n constraints. Another constraint that relates the estimated subject density to the known and measurable quantities is the correlation constraint, or equation (8). These n+1 constraints are to be satisfied by varying a total of n+3 unknowns, namely, α,β,σ and $\rho_s$. The solution is therefore not unique, and some form of regularization is required.

In the preferred embodiment, regularization is numerically performed by minimizing a cost function with respect to parameters α,β, and σ, such as the following cost function:

$$W = \Sigma_i \left|\frac{\partial \tilde{\rho}_s}{\partial \alpha}\right|_i^2 (\alpha - \alpha_1)^2 + \Sigma_i \left|\frac{\partial \tilde{\rho}_s}{\partial \beta}\right|_i^2 (\beta - \beta_1)^2 + \quad (9)$$

$$\Sigma_i \left|\frac{\partial \tilde{\rho}_s}{\partial \sigma}\right|_i^2 (\sigma - \sigma_1)^2 + \lambda \Sigma_R |C_R|^2$$

where $\alpha_1,\beta_1$ and $\sigma_1$ are initial parameter values, i represent the pixels, and R represents subregions of the image as described in more details below. The partial derivatives of $\rho_s$ to the parameters are calculated from equations (6) and (5), and are evaluated at the initial parameter values and fixed during minimization. The partial derivatives may be approximated by finite differences. λ is a coefficient representing the relative weight of the cost terms. The parameter λ is set at a fixed value during minimization, and is adjusted until the minimization yields a solution $\rho_s$ such that the sum $\Sigma|C_R|^2$ falls within an acceptable range as described in more details below.

The first three terms in the cost function associated with α,β, and σ represent a requirement that the parameters determined by the minimization not deviate significantly from their initial values. The initial values $\alpha_1, \beta_1$, and $\sigma_1$ used in the cost function preferably reflect the expected physical properties of the subject relevant to the scatter-glare effects, and the properties of the imaging system, such as imaging geometry. Such values used may be typical values for these parameters as determined by other correction techniques which use the same convolution model for the scatter-glare effects, such as by using beam stops. They may be obtained from a typical patient or by averaging over several patients. These terms as written in partial derivatives to the parameters prevent linear degeneracies from allowing the solution $\alpha, \beta$, and $\sigma$ to wander far from physically sensible values. Linear degeneracies reflect the fact that the effects of parameters $\alpha, \beta$, and $\sigma$ may not be entirely independent, and that each parameter may wander far away from its initial value (which is the physically sensible value) yet the combined effect of all parameters still produce a low correlation between the subject and the phantom.

The last term of the cost function of equation (9) represents the requirement that the correlation between the calibration phantom and the subject density be preferably small. In the regularization process of the preferred embodiment, the image is divided into a plurality of subregions of the image as represented by R in equation (9), and the correlation coefficient for each individual subregion are calculated, squared, and summed up. The number of subregions may be four (two by two), or other numbers. Subdividing the image and calculating the correlation in each region separately reduces the possibility that subregions of the image have chance correlations with the phantom which cancel each other when the correlation coefficient of the entire image is calculated.

The mean expected value for the sum $\Sigma|C_R|^2$, denoted $<\Sigma|C_R|^2>$, is determined in advance for a particular phantom and a particular division of the image into subregions. For example, if the image is divided into R subregions of equal sizes, the theoretical mean expected value $<\Sigma|C_R|^2>$ is $R^2/n$ for a calibration phantom having uncorrelated Gaussian distributed random noise as described hereinbefore. Empirically, the mean expected value of the sum for the particular phantom and the particular image division may be determined by calculating the average correlation between the phantom and subject images that have been corrected for scatter-glare effects using other techniques, as described above.

Figure 2:
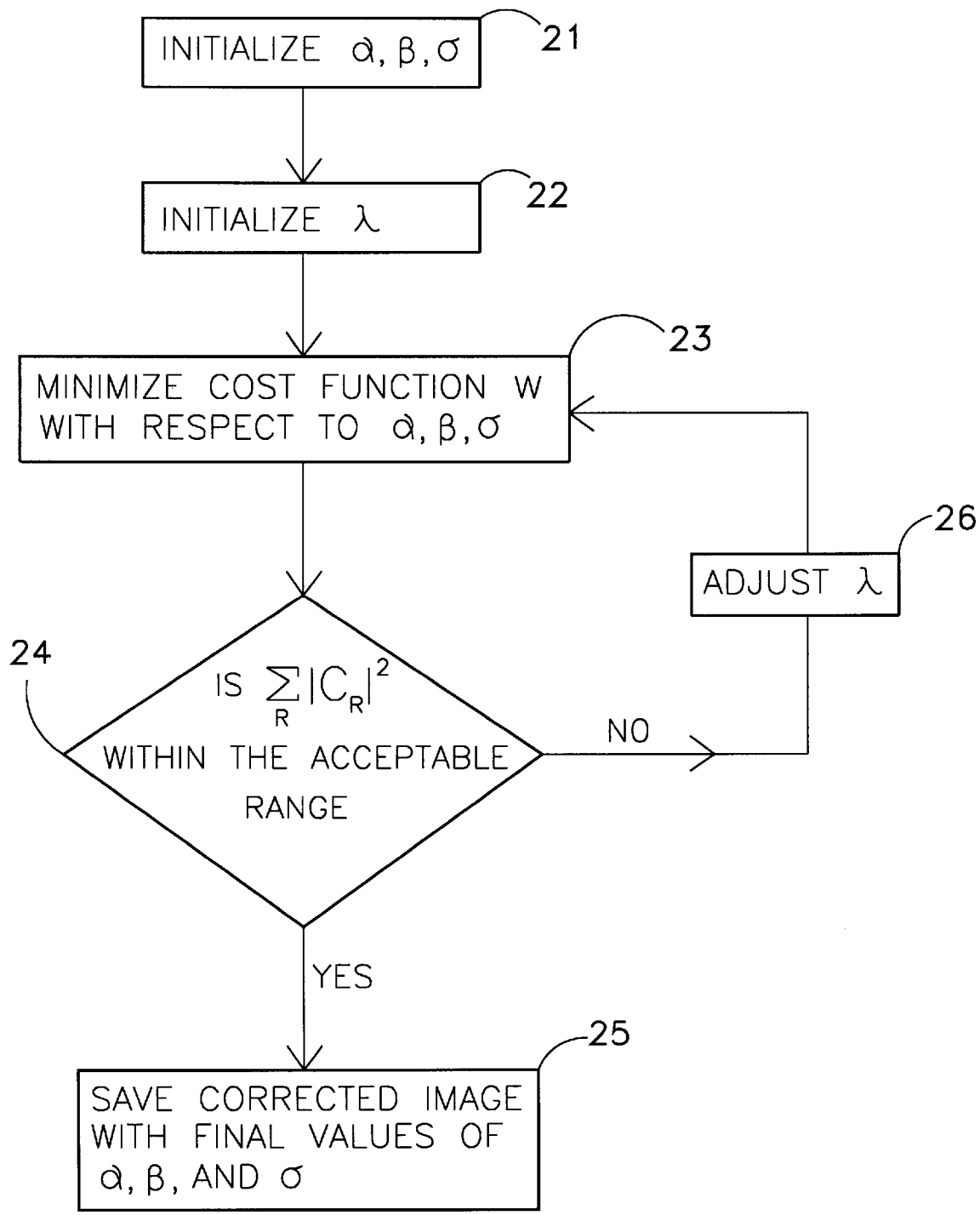
FIG. 2 is a block diagram of the regularization technique according to a preferred embodiment of the present invention.

FIG. 2 is a flow chart of the regularization process according to the preferred embodiment. The parameters $\alpha, \beta$, and $\sigma$ are initialized in step 21, followed by the initialization of the weighting constant $\lambda$ in step 22. The initial values $\alpha_1, \beta_1$, and $\sigma_1$ are set at the values for a typical or average patient, as described above. The initial value of $\lambda$ is not critical, and may be set at, for example, 1. After initialization, the cost function is minimized with respect to parameters $\alpha, \beta$, and $\sigma$ in step 23. Minimization is performed numerically using a standard technique well known in the art, such as the Davidon-Fletcher-Powell algorithm as described in, for example, Press, Flannery, Teukolsky and Vetterling, NUMERICAL RECIPES (Cambridge University Press, 1986). The cost function is evaluated using equations (5) and (6), when the partial derivatives to the parameters are approximated by finite differences and are evaluated at the initial parameter values $\alpha_1, \beta_1$ and $\sigma_1$. In evaluating the cost function, standard two-dimensional fast Fourier transform (FFT) and inverse FFT techniques are used.

After a minimum is reached, the sum of square correlations $\Sigma|C_R|^2$ is evaluated in step 24 to determined whether it falls within an acceptable range around the mean expected value $<\Sigma|C_R|^2>$ as established above. If the sum $\Sigma|C_R|^2$ falls outside of the acceptable range, such as 5% on either side of the mean expected value, then the value of the weighting constant $\lambda$ is adjusted (in step 26) to a new value $\lambda_{new}$, for example, $$\lambda_{new} = \lambda_{old}(\Sigma|C_R|^2/<\Sigma|C_R|^2>) \quad (10)$$

where $\lambda_{old}$ is the old $\lambda$ value used in the previous minimization process. Other $\lambda$ adjustment methods may be used; however, the adjustment must be in the appropriate direction determined by the value of the sum $\Sigma|C_R|^2$. Generally, if the sum falls outside of the acceptable range and is greater than the mean expected value, $\lambda$ is usually increased to give the $\Sigma C_R^2$ term more weight in the cost function. If the sum falls outside of the acceptable range and is less than the mean expected value, $\lambda$ is usually decreased to give the $\Sigma|C_R|^2$ term less weight in the cost function.

The minimization procedure is then repeated in step 23 using the new $\lambda$ value in the cost function. The process of adjusting $\lambda$ and minimizing the cost function is repeated until a $\lambda$ value is found such that the sum $\Sigma|C_R|^2$ falls within the acceptable range when the cost function is minimized. When this occurs, the minimization process is terminated, and the subject density distribution $\rho_s$ calculated in the last cycle of minimization is saved as the optimum subject density distribution, together with the optimum parameters, in step 25. This density distribution gives the restored image (the non-uniform component) from which scatter-glare component of the subject and the calibration phantom, as well as the primary image of the phantom, have been removed.

Because the above regularization technique adjusts the weighting coefficient $\lambda$ and minimizes the cost function while holding $\lambda$ fixed, it is possible that not a single $\lambda$, but $\lambda$ values within a range will produce the result that the sum $\Sigma|C_R|^2$ falls within the acceptable range when the cost function is minimized for that $\lambda$ value. This corresponds to a plurality of sets of parameter values $\alpha, \beta$ and $\sigma$, all of which satisfying the above regularization requirements. These sets of $\alpha, \Gamma$ and $\sigma$ values are all considered acceptable and are not discriminated.

The regularization technique described above may also be used to optimize other acquisition parameters, such as beam hardening and blurring due to finite x-ray aperture size. Beam hardening is an artifact arising from the wavelength dependence of x-ray absorption coefficient of matter. X-rays of longer wavelengths (softer x-rays) are absorbed more by the same material than harder x-rays are, causing the relationship between the thickness h of the absorbing object and its x-ray absorption density $\rho$ to deviate from a linear relationship. This effect may be empirically modeled by including a linear variation with the primary density in the proportionality constant $\mu$ between the thickness h and the x-ray density $\rho$:

$$\rho = \mu h \quad (11)$$

and $$\mu = \mu_0 + \eta \rho_p, \quad (12)$$

where $\mu_0$ and $\eta$ are constants. The parameters $\mu_0$ and $\eta$ may be determined empirically, or may be optimized in the regularization process. If these parameters are included in the regularization, then the regularization is based on the phantom thickness $h_c$ and effective subject thickness $h_s = \rho_s/\mu$, rather than x-ray densities $\rho_c$ and $\rho_s$. Further, the calibration phantom should be constructed from a material with absorption characteristics similar to that of the x-ray contrast material used in the patient. For example, if iodine is used as the x-ray contrast material, tin is preferably used to construct the calibration phantom.

An alternative method for reducing the beam hardening artifact is to construct the calibration phantom from opaque specks narrower than the x-ray aperture but thicker in the x-ray direction than the half-value thickness (the thickness of a material which attenuates the x-ray beam to a half of its incident intensity) for diagnostic energy photons, which is less than 0.17 mm Pb for 70 keV photons. The specks are preferably elongated rods or wires and aligned with the fan beam of x-rays. Such a phantom would attenuate x-rays without changing the x-ray energy spectrum.

Effects of image magnification and blurring may also be corrected using the regularization process. Magnification of an object refers to the relationship between the actual size of the object and the size of the image on the x-ray detector. Blurring refers to half-shadows of an object formed on the image due to the finite size of the aperture of the x-ray source. The amounts of magnification and blurring are dependent upon the distances from the x-ray aperture to the object (subject or phantom) and from the object to the x-ray detector. The calibration phantom and the subject (patient) are typically placed at different distances from the x-ray source and the detector, causing their respective images to have different magnification and blurring. The effects of magnification and blurring of the calibration phantom may also be modeled, and the model parameters, such as the x-ray aperture size and the source-to-image-intensifier distance, may be optimized in the regularization process. When the magnification and blurring effects are included in the regularization, the regularization is based on the density distribution of the calibration phantom defined at the position of the phantom, rather than the density distribution defined at the x-ray image plane. The subject density distribution may be defined either at the image plane or the subject location. Thus, the regularization technique described here may be carried out using either the density distributions defined at the image plane, or the density distributions defined at the respective locations of the subject and the phantom.

Although a preferred embodiment is described in detail, it should be apparent to those skilled in the art that variations in apparatus setup and modeling techniques are possible. For example, the calibration phantom may be physically constructed in a variety of ways to give a desired x-ray density distribution. Further, other forms of response function, cost function, or minimization techniques than described herein may also be employed in the regularization process.

In addition, other techniques may be utilized to improve the performance of scatter-glare removal using the regularization technique of the preferred embodiment. For example, during diagnostics, multiple temporal images are often obtained from a patient. Since the response function parameters and other acquisition parameters should remain the same, they may be optimized globally using all of the temporal images while giving multiple temporal images free of scatter-glare effects. This improves the statistics for the parameter optimization. Further, the calibration phantom may be shifted and/or rotated between successive temporal images to minimize chance correlation between the calibration phantom and the subject.

Moreover, the calibration phantom may be placed at various positions along the x-ray beam path depending on what effects are to be corrected. To correct for both scatter and glare, the calibration phantom is preferably placed between the x-ray source and the patient, so that the image of the phantom is subject to the scatter effect due to the patient. To correct for veiling glare only, the phantom is preferably placed in front of the image intensifier but behind the subject so that only veiling glare effect is present for the phantom. Furthermore, two phantoms may be used to correct separately for scatter and veiling glare. One phantom placed in front of the image intensifier may be used to perform veiling glare correction independent of scatter, and a second phantom may be placed between the x-ray source and the subject to correct subsequently for scatter. If scatter and glare are separately corrected, the response functions used are preferably exponential for veiling glare and Gaussian for scatter.

Although a calibration phantom density distribution having simulated random noise is described, other calibration phantoms having highly structured x-ray density distribution may also be used. One example would be a phantom comprising pie-shaped segments, each segment having a density distribution proportional to the radius with different proportional constants for different segments. Another example would be a phantom comprising a grid, for example a 7 by 7 grid, where each rectangular segment of the grid has a uniform density.

These and other variations should be apparent to those skilled in the art and within the scope of the present invention, which should be determined by the claims.

We claim:

1. A method for recording an x-ray image of a subject having an unknown x-ray density distribution and correcting for image degradation effects, the method comprising:

placing the subject between an x-ray source and an x-ray detector;

placing a reference object between the x-ray source and the x-ray detector, said reference object having a known x-ray density distribution that is substantially spatially uncorrelated to the x-ray density distribution of the subject;

producing digital information representing at least one x-ray image using the x-ray detector, said image comprising images of the subject and the reference object as well as image degradation effects; and processing the digital information until a measurement of the correlation between the density distributions of the reference object and the subject is substantially within a predefined range, whereby the processed digital information represents corrected density distribution of the subject free from the image degradation effects; and displaying the processed digital information.

2. The method of claim 1, wherein the processing of the digital information comprises:

providing a cost function based upon a model for the image degradation effects, said model comprising at least one parameter, said cost function comprising at least one term representing the value of the spatial correlation between the density distribution of the reference object and the corrected subject density distribution;

providing an initial value for each said parameter of the model; and obtaining an acceptable value for each said parameter by minimizing the cost function.

3. The method of claim 2, wherein the image degradation effects are scatter and veiling glare effects.

4. The method of claim 3, wherein the model for the image degradation effects comprises a spatial convolution of a response function with the density distributions of the subject and the reference object.

5. The method of claim 3, wherein the cost function further comprises at least one weighted term representing a deviation of at least one parameter from the initial value.

6. The method of claim 5, wherein the initial value for the parameter reflects the expected physical properties of the subject.

7. The method of claim 5, further comprising adjusting the relative weights of the terms of the cost function so that the term representing the spatial correlation falls within a predetermined acceptable range when the cost function is minimized.

8. The method of claim 7, wherein the predetermined acceptable range is determined based upon knowledge of the range of spatial correlations between the reference object and actual objects having similar physical properties as the subject.

9. The method of claim 2, wherein the produced digital information represents a plurality of x-ray images of the same subject, and wherein one acceptable value for each said parameter is obtained for all images.

10. The method of claim 9, wherein the producing of digital information representing a plurality of x-ray images further comprises changing the relative position or orientation of the reference object with respect to the subject between successive x-ray images.

11. The method of claim 1, wherein the x-ray density distributions of the subject and the reference object are defined in the x-ray detector plane.

12. The method of claim 1, wherein the x-ray density distribution of the reference object is defined at the position of the reference object.

13. The method of claim 1, wherein the x-ray density distribution of the reference object is a random distribution.

14. The method of claim 1, wherein the x-ray density distribution of the reference object is a highly structured distribution.

15. An apparatus for recording an x-ray image of a subject having an unknown x-ray density distribution and correcting for image degradation effects comprising:

an x-ray source for producing a beam of x-rays to be passed through the subject that produces artifacts in addition to image information;

an x-ray detector for producing a digital representation of the x-ray beams passed through the subject including artifact information;

a reference object having a known x-ray density distribution that is spatially substantially uncorrelated to the x-ray density distribution of the subject, said reference object being placed between the x-ray source and the x-ray detector;

a processor responsive to a stored cost function comprising at least one parameter and stored information regarding the reference object, for processing the digital representation produced by the x-ray detector to remove information representing the artifacts from the digital representation to produce a corrected image representation; and display means for displaying the corrected image representation on a medium.

16. The apparatus of claim 15, wherein the known x-ray density distribution of the reference object comprises a density for each pixel of a constant term plus a random term.

17. The apparatus of claim 16, wherein the random term is a sample of Gaussian noise.

18. The apparatus of claim 17, wherein the Gaussian noise has a spectrum, the spectrum having a flat frequency response up to the inverse of the size of the pixel.

19. The apparatus of claim 15 wherein the processor performs:

initializing the parameters of the cost function;

altering the initialized parameters to minimize the cost function.

20. The apparatus of claim 15, wherein the x-ray density distribution of the reference object is a highly structured distribution.

21. An apparatus for recording an x-ray image of a subject having an unknown x-ray density distribution and correcting for artifacts comprising:

an x-ray source for producing a beam of x-rays to be passed through the subject that produces artifacts in addition to subject image information;

an x-ray detector for producing a digital representation of the x-ray beams passed through the subject including artifact information;

a reference object having a known x-ray density distribution that is spatially substantially uncorrelated to the x-ray density distribution of the subject, said reference object being placed between the x-ray source and the x-ray detector; and a processor for processing the digital representation produced by the x-ray detector, the processor being operable to calculate a measurement of the correlation between the density distributions of the reference object and the subject and to produce a corrected subject image representation based on the measurement of the correlation, whereby the corrected subject image representation is substantially free of the artifact information.

22. The apparatus of claim 21, wherein the processor produces the corrected subject image representation by minimizing a cost function having at least one parameter and at least one term representing the measurement of the correlation.

* * * * *